United States Patent [19]

Miller

[11] 4,195,044

[45] * Mar. 25, 1980

[54] HUMIDIFIER-NEBULIZER

[75] Inventor: Kenneth G. Miller, Elk Grove Village, Ill.

[73] Assignee: Respiratory Care, Inc., Arlington Heights, Ill.

[*] Notice: The portion of the term of this patent subsequent to Aug. 29, 1995, has been disclaimed.

[21] Appl. No.: 872,026

[22] Filed: Jan. 24, 1978

Related U.S. Application Data

[63] Continuation-in-part of Ser. No. 826,119, Aug. 19, 1977, Pat. No. 4,110,419, which is a continuation of Ser. No. 569,490, Apr. 18, 1975, abandoned.

[51] Int. Cl.² ............................................... A61M 15/00
[52] U.S. Cl. ................................. 261/142; 128/200.18; 128/200.21; 128/203.26; 261/104; 261/DIG. 65
[58] Field of Search .................. 261/99, 104, 107, 142, 261/DIG. 65; 128/186, 188, 193, 194

[56] References Cited

U.S. PATENT DOCUMENTS

| | | | |
|---|---|---|---|
| 1,267,761 | 5/1918 | Goodfellow | 261/192 |
| 3,724,454 | 4/1973 | Brown | 128/194 |
| 3,874,379 | 4/1975 | Enfield et al. | 261/DIG. 65 |
| 3,892,235 | 7/1975 | Van Amerongen et al. | 261/DIG. 65 |
| 3,916,891 | 11/1975 | Freytag et al. | 261/DIG. 65 |
| 3,944,635 | 5/1976 | Siegenthaler | 128/194 |
| 3,990,442 | 11/1976 | Patneau | 128/194 |
| 4,110,419 | 8/1978 | Miller | 261/DIG. 65 |

FOREIGN PATENT DOCUMENTS 187947 12/1966 U.S.S.R. .......................... 261/DIG. 65

*Primary Examiner*—Frank W. Lutter
*Assistant Examiner*—Gregory N. Clements
*Attorney, Agent, or Firm*—Eric P. Schellin

[57] ABSTRACT

A cylindrical cartridge having a housing containing a replenishable water supply is employed as a water supply source for producing an aerosol with an oxygen stream for inhalation therapy through the agency of a nebulizer adapter which couples pressurized oxygen to the water cartridge. A primary venturi-type insert member is disposed uprightly within a vertical tubular portion of the cartridge. The venturi draws water from the water supply and directs atomized droplets of water and oxygen into a mixing chamber. The aerosol flows out of the cartridge through an outlet nozzle. The cartridge is an elongated housing having a capillary active cylindrical absorption surface means internally whereby water is drawn up along the cartridge's cylindrical body wall which serves as an evaporating surface. The aerosol containing oxygen is humidified by being further charged with evaporated water from the capillary absorption means. Suitable egress port means is provided to which a flexible tube is connected. The tube is then suitably directed to a patient in a conventional manner. The cartridge has a metal wall portion so that when it is associated with a heater the water in the absorption means may be more readily heated by an electric heater. By combining the concept of nebulization and humidification there is achieved an extremely high rate of water content in the gases distributed to a patient.

12 Claims, 3 Drawing Figures

HUMIDIFIER-NEBULIZER

CROSS REFERENCE TO PRIOR FILED APPLICATION

This application is a continuation-in-part application of Ser. No. 826,119 filed Aug. 19, 1977, now U.S. Pat. No. 4,110,419 issued Aug. 29, 1978, which in turn is a continuation of abandoned application Ser. No. 569,490 filed Apr. 18, 1975.

BACKGROUND OF THE INVENTION

The present disclosure relates to inhalation therapy and more particularly to aerosol-producing means in the form of an improved nebulizer for attachment to a cartridge.

As indicated in U.S. Pat. No. 3,711,721, issued Nov. 13, 1973, inhalation therapy is the medical art of treating with oxygen or a mixture of oxygen and air having a high moisture content. Several classes of devices, including atomizers and humidifiers, are adapted for effecting such treatments. With respect to atomizers, or nebulizers as they are often called, a heretofore known system for inhalation therapy comprises a container for pure water which has means enabling operation of the container in one of several modes. An adapter fitting, comprised of a venturi-type member, when associated with the enabling means, adapts the container as a nebulizer reservoir and by itself provides nebulized water in the sense that small droplets of water are carried by the oxygen. A type of improved venturi can be seen from U.S. Pat. No. 3,915,386 issued Oct. 28, 1975. This just mentioned patent and the aforementioned patent are owned by the same assignee as in the present application.

In U.S. patent application Ser. No. 569,490 filed Apr. 18, 1975 of Kenneth G. Miller entitled DISPOSABLE CARTRIDGE HUMIDIFIER, now abandoned and the continuation therefore Ser. No. 826,119, filed Aug. 19, 1977, there is therein disclosed an ingenious cartridge humidifier. The subject matter of these applications are incorporated by reference. The applicant discloses an elongated generally cylindrical cartridge. It has a bottom cap and a top cap, both of which may be constructed of plastic. The two caps are joined by a cylindrical body portion which, to obtain good heat exchange properties, is constructed of a metal, such as aluminum. An electrical heater is provided which has a large bore therethrough into which the aforementioned cartridge is positioned and retained. Suitable tnermostatic controls are provided. Internally with respect to both the bottom cap and the cylindrical body portion cylindrical capillary active member is provided with a diameter sufficient to be in essential contact with the inner wall of the body portion whereby the capillary active member is in excellent heat exchange position with the heater. While the cartridge may be supplied with a fixed quantity of water for humidification it has been found to be particularly efficacious to supply water in a replenishable manner from a supply reservoir which may be an inverted bottle of water. The bottle and the heater may be suitably bracketed together whereby the entire thusly constructed unit may be suitably mounted. The bottom of the cartridge and the bottle containing a supply of water are fluidly connected by suitable egress and ingress ports and a connecting tube to provide an inverted siphon to continuously supply water from the bottle to the cartridge as it is removed therefrom. The water in the cartridge wets the capillary active member to thereby provide a large area for evaporating water than would be possible if the member were not present. The upper cap is provided with a concentrically tube to which a conduit supplying oxygen or air under pressure is supplied. The said tube has a downwardly depending extension that extends concentrically into the mentioned body portion but terminates above the level of the supplied water. In this manner the supplied gas is directed downwardly into the aforementioned body portion. The top cap is provided with an egress port which is located transverse to the axis of the cartridge. The port is connected to flexible conduit which is designed to distribute the humidified gas to a patient. The egress port is in communication with an annular space around the mentioned downward extending tube of the upper cap. In this manner the gases are first directed downwardly through the said tube and then upwardly through the mentioned annular space to the egress port.

While this arrangement of ports has been found to be enormously useful in supplying high volume of humidified gases to a patient, it has been found to be somewhat deficient under some occasions when even larger quantities of moisture must be distributed to the patient wherein the gas has also been warmed so that it is more readily acceptable by the patient and is also somewhat more beneficial.

SUMMARY OF THE INVENTION

The present invention is therefore concerned with the provision of breathable inhaled gases that are moisture laden with a great quantity of water. The water carried by the gases are both obtained as by evaporation and also nebulization so that the gases possess entrained small droplets of water. This is achieved by employing a cartridge of the type mentioned in the aforementioned application for humidification and providing a nebulizer in an appropriate and novel manner. The nebulizer takes the form of a venturi adapter having a tubular member which extends into the aforementioned supply of water located in the cartridge. The venturi adapter is positioned at the top of the concentric tube and is partially external thereof. The venturi adapter includes an egress port means to be connected to a tube which in turn is connected to a supply of either air or oxygen under pressure. The venturi adapter includes a constricted downwardly facing orifice through which the gas proceeds. In association and transverse there to is a second orifice from which the water emanates due to the venturi effect produced by the moving gas. The water and gas then impinge against a rounded abutment to further assist in the breaking up of the water into fine droplets.

The gases carrying the droplets of water then pass downwardly into the body of the cartridge in the manner as described. The gases will pick up additional water through evaporation which is enhanced by the fact the gases also become warmer through their sojourn through the cartridge thereby increasing the total quantity of moisture available to the patient.

DETAILED DESCRIPTION OF THE INVENTION

Figure 1:
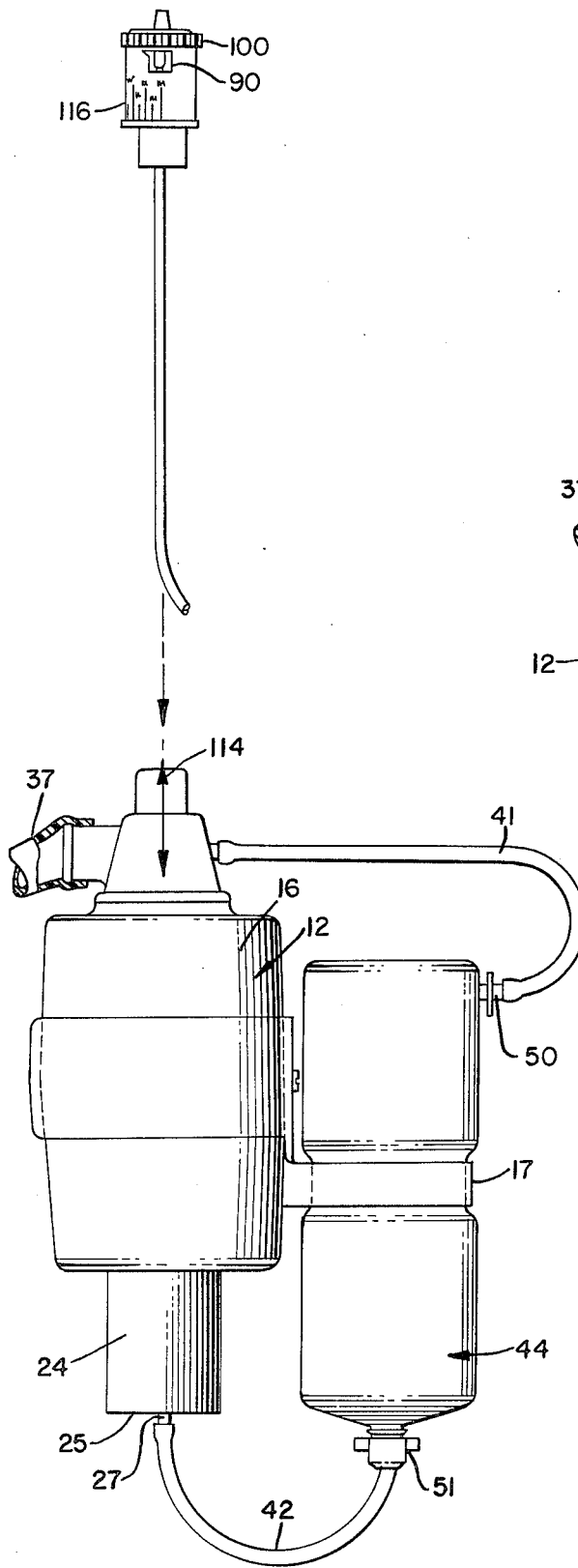
FIG. 1 is a side view of the device of the present invention with the adapter exploded therefrom.

Reference is made to the drawings wherein an illustrative humidifier/nebulizer assembly is generally identified by reference numeral 11. The assembly comprises a combined heater 12 cartridge supporting means. The cartridge 13 may be disposable or semi-disposable and is used in conjunction with a disposable water bottle 14.

The combined heater and cartridge supporting means may comprise any suitable jacket type heater such as an open end metal cylindrical sleeve 15 provided with a suitable resistance heating element, and a suitable thermostatic control (not shown) of any well known type which in turn is connected to a conventional source of electricity. The sleeve 15 may be fabricated from brass tubing or the like, having an exemplary diameter of 2⅛ inches, a 0.051 wall thickness and a length range of approximately 5"–7" or whatever dimension may be warranted to meet certain output conditions. A 100-watt band type heater element in conjunction with the sleeve 15 was found to perform very well, and was connected in a conventionally known manner with a single bi-metallic thermostat which may be suitably set to 185° F., to regulate the temperature of the humidified gases passing through the apparatus.

Sleeve 15 is encased in the illustrated open-ended manner within a preferably insulated housing shell 16 of any suitable rigid material. The thermostat and related heater controls (not shown) may be housed within a lateral projection on the heater, for instance. Any suitable form of an electric switch may be used therein to initially energize the heating element. The housing shell 16 is further preferably provided with suitable support means (not shown) by which the device may be suitably suspended or otherwise supported for inhalation therapy use together with a preferred form of the cartridge.

Additionally, housing shell 16 is preferably provided with bracket means 17 to support within a suitable prepared water supply thermoplastic bottle 14 in predetermined relationship to be further explained hereinafter. One type of such water supply bottle 14 with which the system hereof is designed to work, is the aseptically prefilled liquid bottle known as CONCHA ®, preferably the CONCHA ® 1000 (1000 ml) marketed by Respiratory Care, Inc., of Arlington Heights, Illinois 60004. The manner for encasing the heater sleeve 15 in the stated open-ended manner is such that the cylindrical cartridge 13 can be readily inserted into the open top end thereof, with access provided via the open bottom end for operative connection with the bottle 14.

Figure 3:
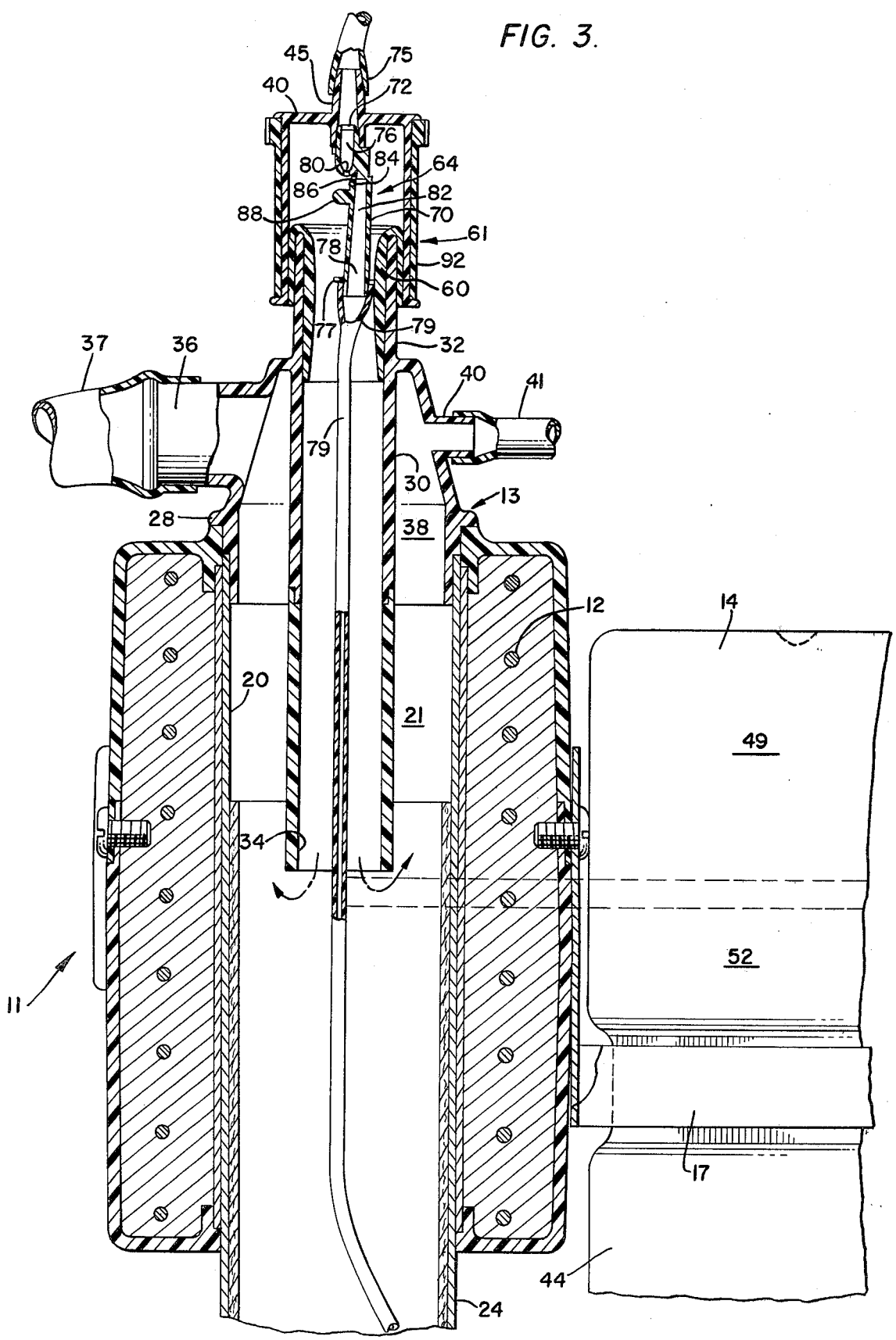
FIG. 3 is a cross-sectional view of the device of the present invention.

A practical form of a disposable or semi-disposable type humidifier cartridge 13, which has performed well, may have a cylindrical body comprised preferably of a metallic main body sleeve member 20, as shown in FIG. 3, which is provided with preferably a non-mettalic top end cap 22 and similar non-mettalic bottom end cap 24. The diameter of the assembled cartridge is such as to have a sliding fit within the heater sleeve 15. An exemplary form of body sleeve 20 may be fabricated of 2" diameter aluminum tubing of appropriate length corresponding generally to the approximate proportions of the illustrative drawings. The end caps 22 and 24 may be fabricated of any suitable rigid type plastic material or the like such as polycarbonate material which will not be adversely affected by the heater sleeve 15.

The cartridge 13 further comprises an absorption column 26 which in one preferred mode, is of a hollow cylindrical form fabricated of an absorbant blotter-like paper material, for example, 3 mm chromatography paper. Absorption column 26 is of a size to lay closely against the inside diameter of the cartridge body, and functions to draw humidifying liquid up into the hollow center portion of the cartridge for evaporating moisture into the gas directed therethrough in a manner to be better described. The vertical length of the absorption column 26 may be greater than shown and may extend substantially the full length of the heater sleeve 15, if desired, for some embodiments.

Upper end cap 22 has its open end mouth portion unitarily joined in any suitable manner to the upper end of intermediate body sleeve 20, and is preferably provided with positioning means such as radial lugs or a flange 28 for limiting the insertion of the cartridge into the heater sleeve 12 in accordance with predetermined limits. Cap 22 is unitarily provided with an axially centered gas inlet tube 30 having an upwardly projecting outer end 32 designed to be connected to the adapter of the present invention as will be hereinafter described. The tube 30 is of a length so that its inner end 34 projects a substantial distance down into and preferably concentrically relative to the cartridge body sleeve 20, but terminates above the level of the water which is either introduced into the bottom portion of the cartridge, or into which the lower end of the cartridge is immersed, as described in the aforementioned pending application, depending upon the embodiment.

Cap 22 is further provided with a gas delivery port and connection pipe 36 extending transversely of the axis of the cartridge. Pipe 36 inwardly communicates with the inner radial space 38 defined between the gas inlet tube 30 and body sleeve 20, and operatively with lower end of said gas inlet tube 30. A flexible tube 37, shown fragmentally in broken outline, is connectable with the external end of the output pipe 36 and is adapted to deliver the treated gas to the patient.

Additionally, in cap 22 there is another transverse pipe connection 40 of relatively smaller diameter than pipe 36, which is adapted to communicate by flexible vent tube 41 with a venting outlet 50 of the particular water bottle and with the aforesaid interior space 38, although the latter set up is not always necessary as the bottle may be merely vented to the atmosphere. Although it is apparent that the vent tube 41 provides for venting of the bottle during delivery of water therefrom via flexible tube 42 into the bottom of the cartridge while maintaining as aseptic assembly by use of sterile tubing and cartridge.

The lower end portion on cap 24 of the cartridge is provided with liquid holding means such as an apertured and nippled transverse end wall 25, which may be made integrally therewith, or may have a slip fit assembly with the open cylindrical end of portion 24. The nipple 27 thereof is adapted to be connected with one end of the flexible delivery tube 42.

The liquid or water bottle means shown in the drawings is preferably one of the aforesaid sealed CONCHA ® units placed in an inverted condition, which unit is disposable sealed plastic container of aseptic water. The container comprises a principal chamber 44. When inverted as noted in the drawings the bottle at its lower end terminates in a neck-like outlet 51 provided with a breachable seal and adapted to be connected with an end of the flexible conduit tube 42. The bottle integrally embodies another neck-like outlet 50 connecting with the air space 49 above the level of the water 51, and possesses a breachable seal adapted to be connected with the flexible conduit 41. In the manner of use as depicted in the drawings, the sealed CONCHA ® is invertedly disposed so that essentially all of the water 52 is confined in the principal chamber 44, from which it is adapted to flow out of outlet 51 via tube 42 and into the lower end of the cartridge via nipple 27 above or substantially coplanar with the bottom transverse wall 25 of the cartridge, in order to assure maximum use of the water during operative use of the apparatus of the present invention.

Preferably both caps 22 and 24 are of a viewable clear, relatively rigid plastic or plastic-like material. The manner of joining the plastic end caps 22 and 24 to the respective ends of the cylindrical sleeve 20 may be as shown, i.e., the mating ends may be complementarily grooved or shouldered so that the I.D. of the metal body sleeve 20 and that of the cap 24 are essentially the same, thereby providing a continuous smooth surface against which the O.D. of the absorption column 26 should engage.

In the concept disclosed in the hereinbefore referenced application, the end 32 is merely attached to a conduit that in turn is connected to a source of air or oxygen. In the present matter the open end 32 is provided for convenience with an insert 60 that enlarges the outer diameter of the end 32 to accept the adapter 61 but also diminishes the internal diameter to enhance the venturi effect of the adapter as will be described below.

References will now be made in more detail to the aformentioned adapter 61 which is essentially a unitary primary venturi insert 64 as seen from FIG. 3. While the details of the venturi assembly can be seen from U.S. Pat. No. 3,915,386 incorporated by reference. The venturi insert 64 has elongated body means 70 constructed so as to form at opposite ends thereof axially offset vertically disposed upper and lower tubular stems 72 and 74 constituting or defining oxygen and water inlet passages 76 and 78, respectively. Upper stem 72 is adapted to have a fluid tight telescopic fit within the downward projecting portion 45 of the center tubular fitting in end wall 40. The upper fully open end of passage 76 is in open fluid flow communication with the oxygen inlet stem 72 and oxygen supply or delivery conduit 75. The passage 76 of the stem 72 is constricted at its lower end to form a small orifice 80.

The water inlet passage or channel 78 is tapered so as to increase in cross-sectional area from its inner and upper end 82 toward its lower end which also connects telescopically in a fluid tight manner into one end of upwardly projecting tube 79. The degree to which the tube 79 is positioned on lower tubular stem 74 is controlled by lug 77. The outer end of tube 79 terminates at or near the bottom of the cartridge. This connection provides fluid communication with the water supply in the cartridge. The narrowed inner end 82 of the water passage 78 terminates generally adjacent and in communication with a horizontally disposed very narrow short venturi water channel 84. Channel 84 terminates in a small terminal orifice 86 similar to and disposed substantially at right angles adjacent to the oxygen inlet orifice 80, thereby constituting the coacting atomizing nozzle orifices.

The atomizing or nebulizing operation is apparent, wherein water is adapted to be drawn up the water inlet channel 78 by the reduced pressure caused by the incoming stream of pressurized oxygen jetting from orifice 80 across the transverse water inlet orifice 86. The water emerging from the venturi channel 84 is broken up into small droplets by the jetting stream of oxygen.

To further assure more complete atomizing of the water droplets, there is a suitable small abutment member 88 disposed adjacently beneath the water orifice 86 and opposite the oxygen orifice 80. Abutment member 88 is depicted as projecting transversely from the side of the venturi body means 70. The incoming oxygen stream then produces an aerosol by this nebulizer fitting by the entrainment of fine water droplets which become further intermixed within the tube 34. As the aerosol flows through the 34 into the main portion of the cartridge the gases pick up additional moisture from the absorbent tube 26 to become humidified as well as constituting an aerosol of fine water droplets. The gases thus produced are then directed upwardly into annular space 38 to tube 36 into flexible tube 37 for distribution to the patient.

Figure 2:
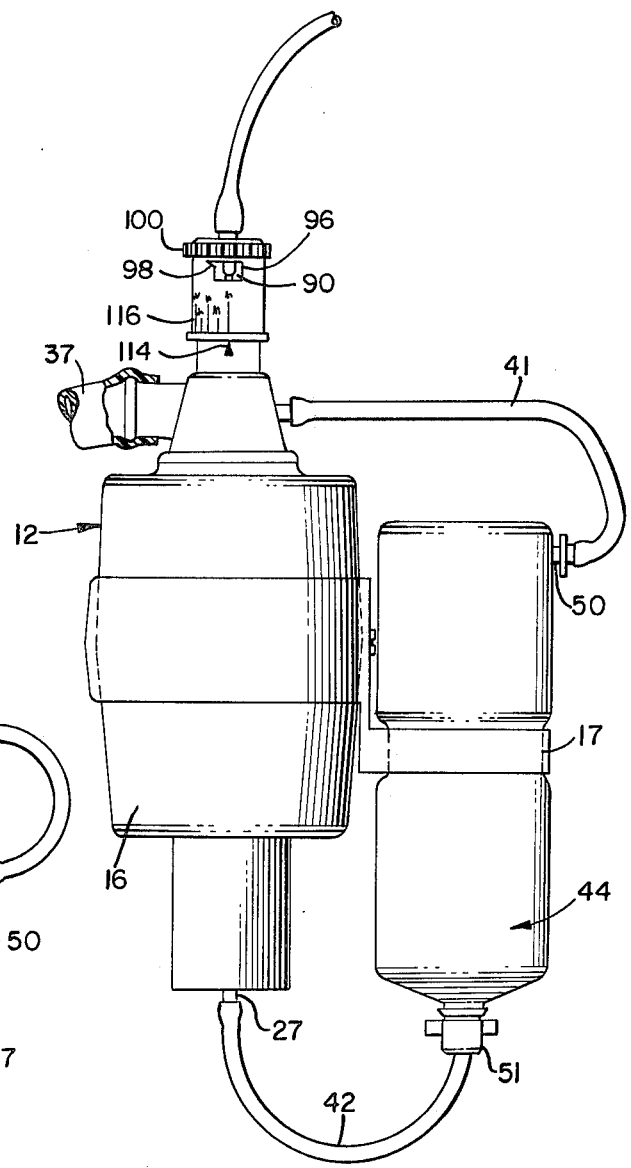
FIG. 2 is the same view with the adapter in place.

While the aerosol producing effect is dependent upon the ingress of oxygen in the manner afore described, means is provided to introduce a controlled amount of ambient air. To dilute the pure oxygen which is adapted to enter the adapter from pipe 75 via center stem 72 and passage 76, the upper tubular adapter has a tubular body portion 91 which is provided with suitable window means, such as a diametrically opposed pair of open windows 90, 90 of predetermined area (one window 90 can be seen from FIGS. 1 and 2). Ambient gases or the atmospheric air may then be entrained in a regulated manner through the window 90 by suitable regulating means, such as rotatable windowed collar means 92. The rotatable collar 92 and tube 32 are provided with cooperative indicia means such as arrow 114 and numeral indicia 116, for designating certain preferred settings. Depending upon the size of the window openings the numeral indicia may be labelled to identify the percentage of mixture of gas and ambient atmosphere.

Collar means 92 as shown, includes an open sleeve body whose cylindrical wall is also preferably provided with a pair of diametrically disposed open windows 96, 96 corresponding to and adapted to align with windows 90, 90 at times. At least one of the windows 96 is provided with an elongated tapering slot 98 shown in FIGS. 1 and 2. Slot 98 serves to provide for a minimal gradual dilution of the oxygen stream by the ambient atmosphere, depending upon the rotatable position of the collar 92. In this illustrative form the collar is provided with a serrated upper portion 100 of slight radial knurlings to provide a manual gripping area to facilitate the rotary adjustment thereof.

As was noted in the above sleeve 60 is provided. The sleeve 60 is in the form of an open ended cylindrical member and internally of the outer end 32 is of much lesser diameter than the outer end 32 of the adapter within which it is disposed. This narrows the throat area of initial atomization and provides increased velocity therethrough of the flow. As shown, the inside diameter of the sleeve 60 is uniform throughout the height but it is contemplated that for some modifications the diameter could vary from larger to smaller commencing at the upper end.

It is apparent from the foregoing that a unique and novelly improved nebulizer adapter fitting has been evolved in accordance with the objectives set forth in the beginning portion hereof.

While one preferred embodiment has been illustrated and described in detail, it is apparent that other changes and modifications may be made by those skilled in the art without departing from the inventive spirit hereof. Reference should be made to the appended claims for the inventive scope covered by this invention.

What is claimed is:

1. Cartridge type humidifying and nebulizing apparatus for humidifying a breathable gas such as oxygen-supplemented air or the like to be inhaled by a patient undergoing inhalation therapy, said apparatus comprising in combination:
   (a) cartridge module means embodying a tubular cartridge main body portion with an inner peripheral wall;
   (b) said cartridge module means also including an upper end portion with cap means unitarily attached to said main body portion and a lower end portion unitarily attached to said main body;
   (c) liquid holding means in association with said lower end portion of said cartridge means for helping retain humidifying liquid in association therewith during operative use of said apparatus;
   (d) said cartridge module means further comprising liquid absorption means including an open center generally tubular liquid-absorption column member with an inner peripheral face constituting an evaporating surface for humidifying liquid disposed generally contiguously within and coextensive with a substantial part of said cartridge main body and lower end portion thereof, said absorption column having a lower end portion adapted to be wetted directly by humidifying liquid when in said liquid holding means, and to convey by absorption liquid upwardly adjacent said evaporating surface;
   (e) said upper-end-portion-mounted cap means of said humidifier cartridge module means of paragraph (b) providing a generally closed air space above the humidifying liquid level of said liquid holding means of paragraph (c);
   (f) said cap means unitarily including a gas inlet feed pipe for directing gas to be humidified into said cartridge main body, at a point above said liquid level, for humidification within said closed air space;
   (g) said gas inlet feed pipe having a venturi insert means including an elongated body with longitudinally disposed upper and lower stem portions that are axially offset and constituting gas and liquid inlet passages respectively, said passages terminating inwardly in transversely adjacent orifices constituting part of the nebulizing means whereby a flow of pressurized gas out of the gas passage orifice past the orifice of said liquid passage creates a suction in the latter adapted to draw liquid therethrough from said liquid in said lower end portion to be aspiratively carried by said gas flow through said gas inlet feed pipe;
   (h) said cartridge module means further including a separate projecting humidified-gas-outlet delivery pipe disposed a substantial distance above said liquid level and in direct fluid communication with said closed air space, said delivery pipe adapted to be connected with an output delivery tube leading to said patient, whereby said gas in said module and delivery tube is maintained in a substantially fully vapor-saturated condition.

2. The cartridge type humidifying and nebulizing apparatus of claim 1 wherein said cartridge main body in paragraph (a) is a predetermined length of cylindrical metal having good heat transfer characteristics; said main body having a lower end portion made of a non-metallic material having a lesser-transfer factor than said metal main body.

3. The cartridge type humidifying and nebulizing apparatus of claim 1 wherein said liquid holding means of paragraph (c) includes a transverse wall sealing the lower end portion of said tubular cartridge body to help constitute said liquid holding means; and liquid inlet means in said transverse wall and adapted to be fluidly connected via conduit means with a liquid outlet means of an external liquid source.

4. The cartridge type humidifying and nebulizing apparatus of claim 1 wherein said cartridge module means is fabricated to be of a disposable character, with the main body portion having a greater heat-transfer factor than said upper and lower end portions on said main body.

5. The cartridge type humidifying and nebulizing apparatus of claim 3 wherein said source is a reservoir including aseptic liquid presealed within a readily attachable/detachable container of disposable character, and said container's openable means includes thread means for threaded connection with complementary thread means on said lower portion of the main cartridge body.

6. Cartridge type humidifying and nebulizing apparatus for humidifying and heating a breathable gas such as oxygen-supplemented air or the like to be inhaled by a patient undergoing inhalation therapy, said apparatus comprising in combination:
   (a) heating module means for heating the air to be steadily delivered to a patient, comprising an upright generally tubular sleeve-type heat-conducting body;
   (b) cartridge module means embodying a tubular cartridge main body portion with an inner peripheral wall and adapted to be axially received and disposed generally concentrically within and heated by said heating module means;
   (c) said cartridge module means also including an upper end portion with cap means unitarily attached to said main body portion, said main body via a lower end portion thereof adapted to be removably insertable with a relatively close slip fit within the body of said heater module means and a lower end portion unitarily attached to said main body;
   (d) liquid holding means in association with said lower end portion of said cartridge module means for helping retain humidifying liquid in association therewith during operative use of said apparatus;
   (e) said cartridge module means further comprising liquid absorption means including an open center generally tubular liquid-absorption column member with an inner peripheral face constituting an evaporating surface for humidifying liquid disposed generally contiguously within and coextensive with a substantial part of said cartridge main body and lower end portion thereof, said absorption column having a lower end portion adapted to be wetted directly by the humidifying liquid when in said liquid holding means, and to convey by absorption liquid upwardly adjacent said evaporating surface;
   (f) said upper-end-portion-mounted cap means of said humidifier cartridge module means of paragraph (c) providing a generally closed air space above the humidifying liquid level of said liquid holding means of paragraph (d);

(g) said cap means unitarily including a gas inlet feed pipe for directing gas to be humidified into said cartridge main body, at a point above said liquid level, for humidification and heating within said closed air space;

(h) said gas inlet feed pipe having a venturi insert means including an elongated body with longitudinally disposed upper and lower stem portions that are axially offset and constituting gas and liquid inlet passages respectively, said passages terminating inwardly in transversely adjacent orifices constituting part of the nebulizing means whereby a flow of pressurized gas out of the gas passage orifice past the orifice of said liquid passage creates a suction in the latter adapted to draw liquid therethrough from said liquid in said lower end portion to be aspiratively carried by said gas flow through said gas inlet feed pipe;

(i) said cartridge module means further including a separate projecting humidified-gas-outlet delivery pipe disposed a substantial distance above said liquid level and in direct fluid communication with said closed air space, said delivery pipe adapted to be connected with an output delivery tube leading to said patient, whereby said gas in said module and delivery tube is maintained in a substantially fully vapor-saturated condition and at a heated temperature not exceeding predetermined safe limits during operative use of said apparatus;

(j) wherein said cartridge main body in paragraph (b) is a predetermined length of cylindrical metal tube having good heat transfer characteristics; said main body having a lower end portion made of a non-metallic material having a lesser heat-transfer factor than said metal main body.

7. The apparatus of claim 6 wherein said upper end portion and cap means of paragraph (c) also is of nonmetallic material, said upper and lower end portions being fabricated of a transparent rigid plastic-like material.

8. Cartridge type humidifying and nebulizing apparatus for humidifying and heating a breathable gas such as oxygen-supplemented air or the like to be inhaled by a patient undergoing inhalation therapy, said apparatus comprising in combination:

(a) heating module means for heating the air to be steadily delivered to a patient, comprising an upright generally tubular sleeve-type heat-conducting body;

(b) cartridge module means embodying a tubular cartridge main body portion with an inner peripheral wall and adapted to be axially received and disposed generally concentrically within and heated by said heating module means;

(c) said cartridge module means also including an upper end portion with cap means unitarily attached to said main body portion, said main body via a lower end portion thereof adapted to be removably insertable with a relatively close slip fit within the body of said heater module means and a lower end portion unitarily attached to said main body;

(d) liquid holding means in association with said lower end portion of said cartridge module means for helping retain humidifying liquid in association therewith during operative use of said apparatus;

(e) said cartridge module means further comprising liquid absorption means including an open center generally tubular liquid-absorption column member with an inner peripheral face constituting an evaporating surface for humidifying liquid disposed generally contiguously within and coextensive with a substantial part of said cartridge main body and lower end portion thereof, said absorption column having a lower end portion adapted to be wetted directly by the humidifying liquid when in said liquid holding means, and to convey by absorption liquid upwardly adjacent said evaporating surface;

(f) said upper-end-portion-mounted cap means of said humidifier cartridge module means of paragraph (c) providing a generally closed air space above the humidifying liquid level of said liquid holding means of paragraph (d);

(g) said cap means unitarily including a gas inlet feed pipe for directing gas to be humidified into said cartridge main body, at a point above said liquid level, for humidification and heating within said closed air space;

(h) said gas inlet feed pipe having a venturi insert means including an elongated body with longitudinally disposed upper and lower stem portions that are axially offset and constituting gas and liquid inlet passages respectively, said passages terminating inwardly in transversely adjacent orifices constituting part of the nebulizing means whereby a flow of pressurized gas out of the gas passage orifice past the orifice of said liquid passage creates a suction in the latter adapted to draw liquid therethrough from said liquid in said lower end portion to be aspiratively carried by said gas flow through said gas inlet feed pipe;

(i) said cartridge module means further including a separate projecting humidified-gas-outlet delivery pipe disposed a substantial distance above said liquid level and in direct fluid communication with said closed air space, said delivery pipe adapted to be connected with an output delivery tube leading to said patient, whereby said gas in said module and delivery tube is maintained in a substantially fully vapor-saturated condition and at a heated temperature not exceeding predetermined safe limits during operative use of said apparatus;

(j) wherein said liquid holding means of paragraph (d) including a transverse wall sealing the lower end portion of said tubular cartridge body to help constitute said holding means; and liquid inlet means in said transverse wall and adapted to be fluidly connected via conduit means with a liquid outlet means of an external liquid reservoir associated with said heating module means.

9. The apparatus of claim 8, further including a disposable reservoir of aseptic liquid sealed therein, said disposable reservoir having a liquid outlet pipe and operatively connected with said liquid holding means by means including said liquid outlet pipe; means for detachably mounting said reservoir externally on said heating module means; and separate conduit venting means operatively connected with and for venting said sealed liquid of said disposable reservoir in an aseptically sealed manner with an upper portion of said cartridge module body.

10. The apparatus of claim 9 wherein said liquid reservoir is mounted relative to said cartridge module body and to said liquid holding means such that the liquid in said exteriorly disposed liquid reservoir is adapted to be substantially completely transferrable into said liquid holding means for most efficient and waste-free use of said reservoir liquid.

11. A method for humidifying, nebulizing, and heating breathable gas such as oxygen-supplemented air or the like to be inhaled by a patient undergoing inhalation therapy, and method comprising the steps of:
   (a) concentrically disposing tubular heater module means and cartridge-type humidifying and nebulizing module means by inserting said cartridge within said tubular heater means;
   (b) introducing a predetermined amount of humidifying liquid into said humidifying and nebulizing module means having a tubular cartridge body which has an inner peripheral wall, and said module also including liquid absorption means including an upright liquid-absorbing wall member with an inner peripheral face constituting an evaporating surface for humidifying liquid disposed essentially contiguously adjacent a substantial part of said inner peripheral wall with a lower end portion adapted to be wetted by the humidifying liquid; and
   (c) energizing said heater module means which includes an upright heat-conducting open-ended tubular body with means for generating and controlling heat of a predetermined temperature range by closing manual switch means operatively connected therewith;
   (d) introducing a breathable gas under pressure into a first zone in said tubular cartridge through a venturi for drawing a portion of said liquid and nebulizing said liquid in said first zone;
   (e) transporting the resultant gas to a second zone in said tubular cartridge body whereby said gas is humidified;
   (f) thereafter delivering the resultant breathable gas external of said cartridge type humidifying and nebulizing means.

12. The method of claim 11 wherein step (b) includes maintaining a humidifying liquid reservoir in association with said lower end portion of said liquid absorption wall member, and connected with a corresponding lower portion of said tubular humidifying cartridge body for supplying humidifying liquid in wetting association with said liquid absorbing wall member.

* * * * *